United States Patent [19]
Lewis et al.

[11] Patent Number: 5,718,973
[45] Date of Patent: Feb. 17, 1998

[54] TUBULAR INTRALUMINAL GRAFT

[75] Inventors: James D. Lewis, Flagstaff; David J. Myers, Camp Verde, both of Ariz.

[73] Assignee: W. L. Gore & Associates, Inc., Newark, Del.

[21] Appl. No.: 508,213

[22] Filed: Jul. 26, 1995

Related U.S. Application Data

[63] Continuation of Ser. No. 108,967, Aug. 18, 1993, abandoned.

[51] Int. Cl.$^6$ .......................... B29D 22/00; B29D 23/00; B29D 1/08
[52] U.S. Cl. ................... 428/36.5; 428/35.7; 428/36.3; 428/36.92; 428/421; 623/1; 623/11; 623/12
[58] Field of Search .................. 428/35.7, 36.3, 428/36.5, 36.92, 421; 623/1, 11, 12

[56] References Cited

U.S. PATENT DOCUMENTS

| | | | |
|---|---|---|---|
| 2,016,962 | 10/1935 | Flent et al. | 564/471 |
| 2,844,609 | 7/1958 | Tesuro et al. | 204/404 |
| 3,657,744 | 4/1972 | Ersek | 623/11 |
| 3,868,956 | 3/1975 | Alfidi et al | 606/194 |
| 4,130,904 | 12/1978 | Whalen | 623/1 |
| 4,140,126 | 2/1979 | Choudury | 606/194 |
| 4,190,909 | 3/1980 | Ablaza | 623/1 |
| 4,208,745 | 6/1980 | Okita . | |
| 4,304,010 | 12/1981 | Mano | 623/1 |
| 4,313,231 | 2/1982 | Koyamada | 623/1 |
| 4,512,228 | 4/1985 | Balko et al. | 83/355 |
| 4,550,447 | 11/1985 | Seiler, Jr. et al. | 623/1 |
| 4,553,545 | 11/1985 | Maass et al. | 606/198 |
| 4,562,596 | 1/1986 | Kornberg | 623/1 |
| 4,577,631 | 3/1986 | Kraemer | 606/108 |
| 4,655,771 | 4/1987 | Wallsten | 623/1 |
| 4,681,110 | 7/1987 | Wiktor | 606/194 |
| 4,776,337 | 10/1988 | Palmaz | 606/108 |
| 4,787,899 | 11/1988 | Lazarus | 623/1 |

(List continued on next page.)

FOREIGN PATENT DOCUMENTS

| | | |
|---|---|---|
| 0010293 | 4/1980 | European Pat. Off. . |
| 0137605 | 4/1985 | European Pat. Off. . |
| 461791 | 12/1991 | European Pat. Off. . |
| 464755 | 1/1992 | European Pat. Off. . |
| 466518 | 1/1992 | European Pat. Off. . |
| 480667 | 4/1992 | European Pat. Off. . |
| 508473 | 10/1992 | European Pat. Off. . |
| 518704 | 12/1992 | European Pat. Off. . |
| 528039 | 2/1993 | European Pat. Off. . |
| 539237 | 4/1993 | European Pat. Off. . |
| 2288510 | 5/1976 | France . |
| 2333487 | 7/1977 | France . |
| 3918736 | 12/1990 | Germany . |
| 55-36492 | 5/1976 | Japan . |
| 53-67109 | 6/1978 | Japan . |
| 60-172306 | 9/1985 | Japan . |
| 2068827 | 8/1981 | United Kingdom . |
| 9112779 | 9/1991 | WIPO . |
| 9113648 | 9/1991 | WIPO . |

OTHER PUBLICATIONS

New Riverside Dictionary, The Riverside Publishing Company, 1984, p. 196.
Balko A et al., Transfemoral Placement of Intraluminal Polyurethane Prosthesis for Abdomimal Aortic Aneurysm. Jou of Surg Research 1986: 40:305-309.
Chuter T A M et al., Transfemoral Endovascular Aortic Graft Placement. Jour of Vas Surg Aug. 1993: vol. 18(2): 185-197.

(List continued on next page.)

*Primary Examiner*—Kathleen Choi
*Attorney, Agent, or Firm*—Wayne D. House

[57] ABSTRACT

A tubular intraluminal graft for repairing body conduits, made from at least one layer of porous expanded PTFE film that has a microstructure having fibrils oriented in at least two directions which are substantially perpendicular to each other. The tubular intraluminal graft has a wall thickness of less than about 0.25 mm and may have a longitudinally or helically oriented seamline. Additional reinforcing components such as reinforcing ribs or braids may also be provided.

18 Claims, 5 Drawing Sheets

U.S. PATENT DOCUMENTS

| | | | |
|---|---|---|---|
| 4,791,966 | 12/1988 | Eilentropp | 138/154 |
| 4,816,339 | 3/1989 | Tu et al. | 428/421 |
| 4,820,298 | 4/1989 | Leveen et al. | 623/1 |
| 4,877,030 | 10/1989 | Beck et al. | 606/195 |
| 4,878,906 | 11/1989 | Lindermann et al. | 623/1 |
| 4,925,710 | 5/1990 | Buck et al. | 428/34.5 |
| 4,954,126 | 9/1990 | Wallsten | 600/36 |
| 5,009,814 | 4/1991 | Kellensberg et al. | 252/548 |
| 5,078,726 | 1/1992 | Kreamer | 606/194 |
| 5,107,852 | 4/1992 | Davidson et al. | 128/172 |
| 5,122,154 | 6/1992 | Rhodes | 606/198 |
| 5,123,917 | 6/1992 | Lee | 623/1 |
| 5,151,105 | 9/1992 | Kwan-Gett | 623/1 |
| 5,156,620 | 10/1992 | Pigott | 623/1 |
| 5,211,658 | 5/1993 | Clouse | 623/1 |
| 5,236,447 | 8/1993 | Kubo et al. | 623/1 |
| 5,269,810 | 12/1993 | Hull et al. | 607/129 |
| 5,282,847 | 2/1994 | Trescony et al. | 623/1 |

OTHER PUBLICATIONS

Cragg A H, Drake M. D. Percutaneous Femoropopliteal Graft Placement. Radiology 1993; 187(3):643–648.

George P J M et al., Covered expandable metal stent for recurrent tracheal obstruction. The Lancet, Mar. 1990; 335:582–584.

Kato M et al., Development of a chronic endothelialized transcatheter implantable intra–aortic graft. ASAIO Journal 1993; M518–M521.

Lawrence D D et al., Percutaneous Endovascular Graft: Experiment Evaluation. Radiology May 1987; 163(2):357–360.

Mirich D et al., Percutaneously Placed Endovascular Grafts for Aortic Aneurysms: Feasibility Study. Radiology 1989; 170(3):1033–1037.

Parodi J C et al., Transfemoral Intraluminal Graft Implantation for Abdominal Aortic Aneurysms. Annals of Vascular Surg 1991; vol 5(6):491–499.

Preminger T J et al., Transluminal vascular stenting using a Gore–Tex covered stent: An experimental study. Presented at at the congress of Pediatric Cardiology and Cardiac Surgery Jun. 21–25 1993.

Sayers R D et al., Endovascular stenting of abdominal aortic aneurysms. Eur J Vasc Surg 1993; 7:225–227.

Schenck R R and Derman G H. An Intraluminal Silastic Stent for Small Vessel Repair. Orth Clin North Amer. Apr. 1977: 8(2):265–271.

Yoshida H et al., Transcatheter Placement of an Intraluminal Prosthesis for the Thoracic Aorta, A New Approach to Aortic Dissections. ASAIO Transactions 1991; 37:M272–M273.

Yoshioka T et al. Self–Expanding Endovascular Graft: An Experimental Study in Dogs. AJR Oct. 1988; 151:673–676.

TUBULAR INTRALUMINAL GRAFT

This application is a continuation of application Ser. No. 08/108,967 filed Aug. 18, 1993, now abandoned.

FIELD OF THE INVENTION

This invention relates to the field of intraluminal grafts and particularly to thin-wall intraluminal grafts useful as a lining for blood vessels or other body conduits.

BACKGROUND OF THE INVENTION

Conventional vascular grafts have long been used for vascular repair in humans and animals. These devices are typically flexible tubes of woven or knitted polyethylene terephthalate or of porous polytetrafluoroethylene (hereinafter PTFE). Grafts of biological origin are also used, these being typically fixed human umbilical or bovine arteries. These conventional vascular grafts usually require invasive surgical methods that expose at least both ends of the segment of vessel to be repaired. Frequently it is necessary to expose the entire length of the vessel segment. These types of repairs consequently cause major trauma to the patient with corresponding lengthy recovery periods and may result in occasional mortality.

Alternative methods have evolved which use intraluminal vascular grafts in the form of diametrically-expandable metallic stent structural supports, tubular grafts or a combination of both. These devices are preferably remotely introduced into a body cavity by the use of a catheter type of delivery system. Alternatively they may be directly implanted by invasive surgery. The intent of these methods is to maintain patency after an occluded vessel has been re-opened using balloon angioplasty, laser angioplasty, atherectomy, rotoablation, invasive surgery, or a combination of these treatments.

Intraluminal vascular grafts can also be used to repair aneurysmal vessels, particularly aortic arteries, by inserting an intraluminal vascular graft within the aneurysmal vessel so that the prosthetic withstands the blood pressure forces responsible for creating the aneurysm.

Intraluminal vascular grafts provide a new blood contacting surface within the lumen of a diseased living vessel. Intraluminal grafts are not, however, limited to blood vessels; other applications include urinary tracts, biliary ducts, respiratory tracts and the like.

If the intraluminal graft used is of thin enough wall and adequate flexibility, it may be collapsed and inserted into a body conduit at a smaller diameter location remote from the intended repair site. A catheter type of delivery system is then used to move the intraluminal graft into the repair site and then expand its diameter appropriately to conform to the inner surface of the living vessel. Various attachment methods including the use of expandable metallic stents may be used to secure the intraluminal graft at the desired location without the necessity of invasive surgery.

Intraluminal vascular grafts were suggested as early as 1912 in an article by Alexis Carrel (Results of the permanent intubation of the thoracic aorta. Surg., Gyn and Ob. 1912;15:245–248). U.S. Pat. No. 3,657,744 to Ersek describes a method of using one or more expandable stents to secure a flexible fabric vascular graft intraluminally, the graft and stent having been introduced distally and delivered to the desired position with a separate delivery system.

Choudhury, U.S. Pat. No. 4,140,126, describes a similar method of repairing aortic aneurysms whereby a polyethylene terephthalate vascular graft is fitted at its ends with metal anchoring pins and pleated longitudinally to collapse the graft to a size small enough to allow for distal introduction.

Rhodes, U.S. Pat. No. 5,122,154 and Lee, U.S. Pat. No. 5,123,917, describe endovascular bypass grafts for intraluminal use which comprise a sleeve having at least two diametrically-expandable stents. Rhodes teaches that the sleeve material is to be made of conventional vascular graft materials such as GORE-TEX® Vascular Graft (W. L. Gore & Associates, Inc., Flagstaff Ariz.) or Impra® graft (Impra, Inc. Tempe Ariz.). Both the GORE-TEX Vascular Graft and Impra Graft are extruded and longitudinally expanded PTFE tubes. Additionally, the GORE-TEX Vascular Graft possesses an exterior helical wrapping of porous expanded PTFE film. The difficulty with the use of either the GORE-TEX Vascular Graft or the Impra Graft as the sleeve component is that the relatively thick, bulky wall of these extruded, longitudinally expanded PTFE tubes limits the ability of the tube to be contracted into a small cross-sectional area for insertion into a blood vessel. For example, the wall thickness of a 6 mm inside diameter Thin Walled GORE-TEX Vascular Graft is typically 0.4 mm. The thinness of the wall is limited by the difficulty of producing an extruded, longitudinally expanded tube having a thin wall of relatively uniform thickness.

SUMMARY OF THE INVENTION

The present invention is a tubular intraluminal graft comprised of porous expanded PTFE film having a microstructure of nodes interconnected by fibrils, the fibrils being oriented in at least two directions which are substantially perpendicular to each other. These multiaxially-oriented films having either biaxially or multiaxially-oriented fibrils are made by an expansion process as taught by U.S. Pat. Nos. 3,953,566; 4,187,390 and 4,482,516; these patents are herein incorporated by reference. The films are expanded by stretching them in at least two directions. Multiaxially-oriented films include films having biaxially-oriented fibrils that are oriented primarily in two directions that are substantially perpendicular to each other. Multiaxially-oriented films also include films having multiaxially-oriented fibrils wherein the fibrils are oriented in all directions within the plane of the film.

The term expanded is used herein to refer to porous expanded PTFE. The terms expand, expanding and expandable are used herein to refer to diametrically-adjustable intraluminal stents.

Multiaxially-oriented films having either biaxially or multiaxially-oriented fibrils may be made by expanding the film by stretching it in two directions that are substantially perpendicular to each other, for example longitudinally and transversely. Films having multiaxially-oriented fibrils may also be made by expanding the film by stretching it in more than two directions. Conditions that may affect fibril orientation include not only the directions of forces applied during expansion, but also expansion rate, expansion amounts, and the use of either simultaneously or sequentially applied expansion forces.

Because porous expanded PTFE films are typically of greatest strength in the directions parallel to the orientation of the fibrils, an intraluminal graft constructed from these multiaxially-oriented porous expanded PTFE films will have good strength characteristics in all directions. The inventive intraluminal graft has a wall with a thickness of less than about 0.25 mm and preferably less than 0.10 mm. The wall of the graft comprises at least one layer of the multiaxially-oriented porous expanded PTFE film.

The inventive intraluminal graft has good hoop strength because of the multiaxially-oriented film from which it is made. The graft is flexible and collapsible, thereby allowing it to be collapsed to a size much smaller than the full inside diameter. The graft is capable of being implanted into a living body in the collapsed state and can therefore be inserted into a conveniently accessible, smaller diameter portion of a body conduit and then transferred to another, larger diameter portion of the body conduit where it is needed with the use of a catheter type of delivery system. One end of the intraluminal graft is then secured by suitable means such as the use of a metallic expandable stent. The use of the inventive intraluminal graft thus allows for the effective repair of living blood vessels without the trauma typically associated with conventional invasive vascular surgery.

The inventive intraluminal graft may optionally incorporate separate reinforcing ribs intended to serve as additional strength members. The ribs may be either longitudinally oriented or circumferentially oriented as long as they do not prevent the graft from being diametrically collapsed for insertion into the vascular system. These ribs may be in the form of, for example, stringers of PTFE or fluorinated ethylene propylene (hereinafter FEP) of small diameter such as about 0.025 mm to about 0.5 mm. The use of, for example, longitudinally-oriented ribs can add significantly to the longitudinal strength of the graft without appreciably interfering with the ability of the graft to be collapsed in diameter for ease of insertion into a vascular system and then subsequently increased in diameter at a different location within the vascular system. These ribs may easily be incorporated into the graft during construction of the graft, for example, by temporarily attaching the ribs to the surface of a manufacturing mandrel prior to wrapping the mandrel with a layer of porous expanded PTFE film. The mandrel assembly can then be heated adequately to cause the ribs to adhere to the film, after which the mandrel can be removed. The ribs may be located on the luminal surface of the film, on the exterior surface of the film, or between two layers of the film. A braid may also be used as an additional reinforcing component in place of reinforcing ribs.

DETAILED DESCRIPTION OF THE INVENTION

Figure 1:
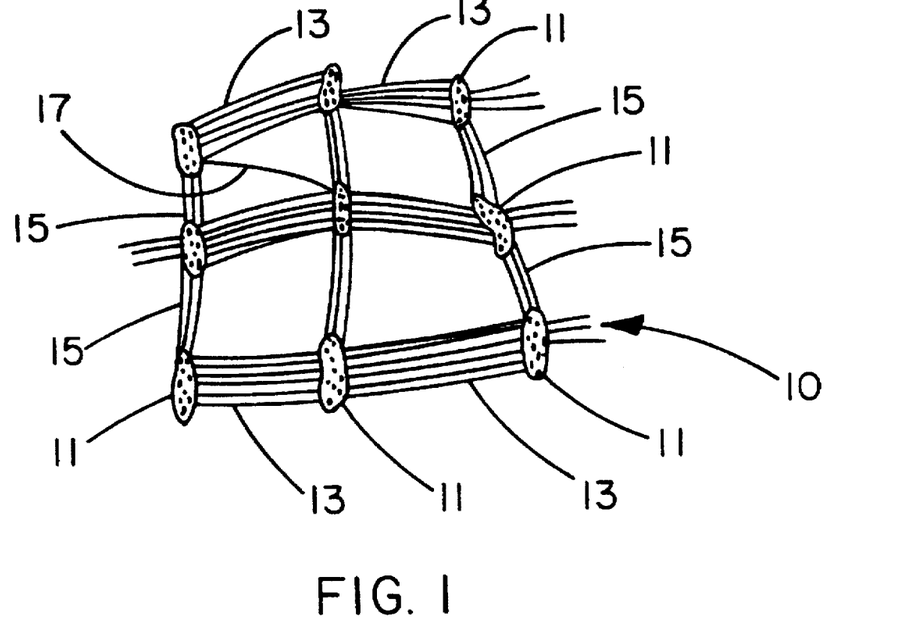
FIG. 1 is an enlarged schematic representation of a multiaxially-oriented porous expanded PTFE film having biaxially-oriented fibrils used to construct the intraluminal graft of the present invention.

FIG. 1 shows an enlarged schematic representation of the surface microstructure of a multiaxially-oriented film 10 having biaxially-oriented fibrils wherein nodes 11 are connected by fibrils 13 and fibrils 15. Fibrils 13 and 15 are oriented respectively in two directions which are substantially perpendicular to each other within the plane of the film. These multiaxially-oriented films having biaxially-oriented fibrils may also contain some fibrils such as fibril 17 that are not parallel to either fibrils 13 or fibrils 15.

Figure 2:
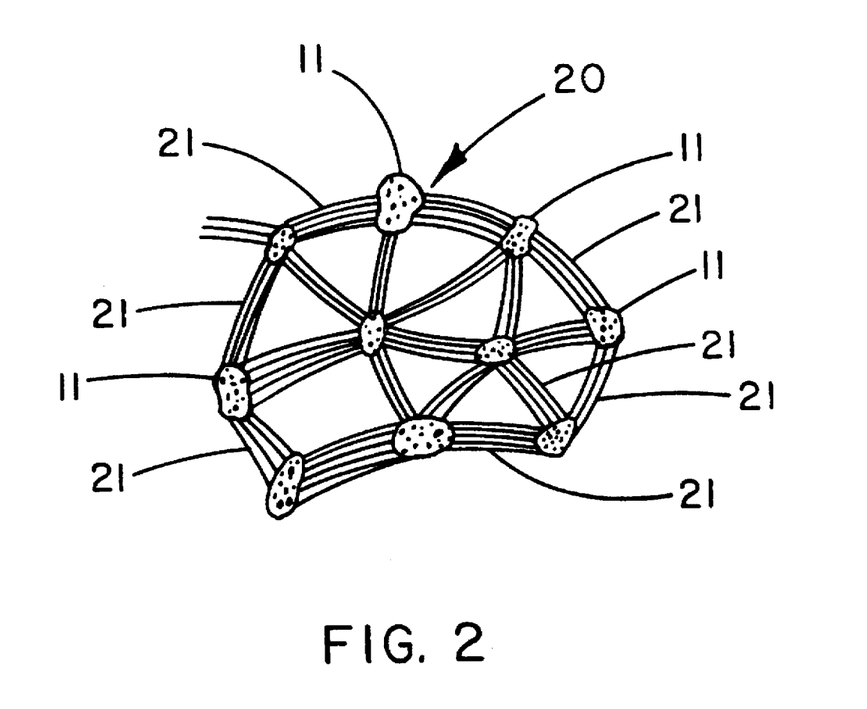
FIG. 2 is an enlarged schematic representation of a multiaxially-oriented porous expanded PTFE film having multiaxially-oriented fibrils used to construct the intraluminal graft of the present invention.

FIG. 2 describes an enlarged schematic representation of the surface microstructure of a multiaxially-oriented film 20 wherein nodes 11 are connected by fibrils 21. The fibrils 21 are multiaxially-oriented fibrils which are oriented in substantially all directions within the plane of the film wherein virtually all fibrils are oriented substantially perpendicular to some other fibrils.

Figure 3:
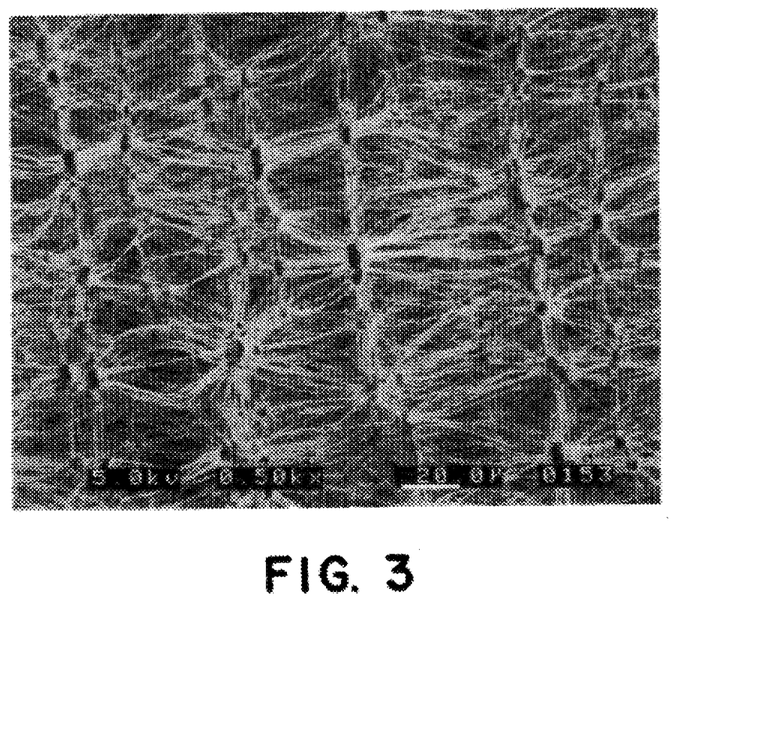
FIG. 3 is a scanning electron photomicrograph ×500 of a multiaxially-oriented porous expanded PTFE film having biaxially-oriented fibrils used to construct the intraluminal graft of the present invention.

FIG. 3 shows a scanning electron photomicrograph of a multiaxially-oriented porous expanded PTFE film having biaxially-oriented fibrils used to construct examples 1 and 2 described below.

Figure 4:
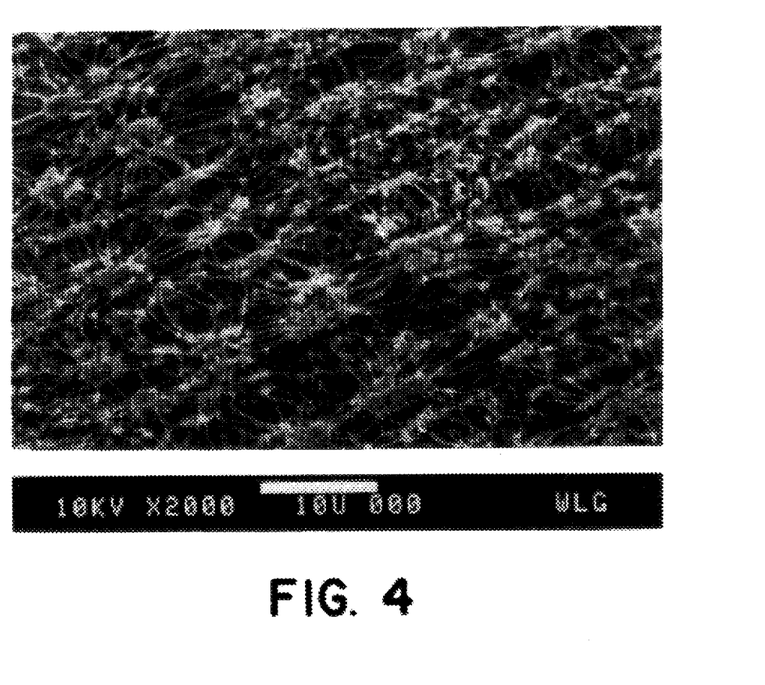
FIG. 4 is a scanning electron photomicrograph ×2000 of a multiaxially-oriented porous expanded PTFE film having multiaxially-oriented fibrils used to construct the intraluminal graft of the present invention.

FIG. 4 shows a scanning electron photomicrograph of a multiaxially-oriented porous expanded PTFE film having multiaxially-oriented fibrils used to construct example 3 described below.

Figure 5:
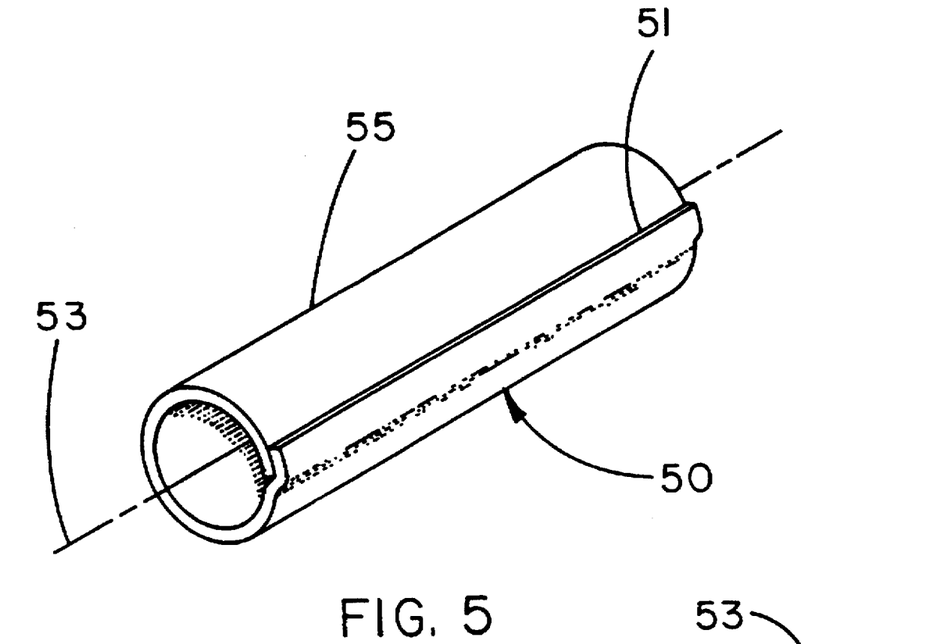
FIG. 5 is a perspective view of an intraluminal graft of the present invention having a longitudinally oriented seamline.

The tubular intraluminal graft is manufactured by wrapping a multiaxially-oriented porous expanded PTFE film around a mandrel and forming a seamline by overlapping adjacent edges of the film. As shown by FIG. 5, the seamline 51 may be longitudinally-oriented so that it is substantially parallel to the longitudinal axis 53 of the graft 50. After the seamline 51 is formed, the film-wrapped mandrel is placed into an oven set above the melt-point of the PTFE film 55 for a time adequate to cause the overlapping edges of the film to adhere to each other. After heating, the film-wrapped mandrel is removed from the oven and allowed to cool. The mandrel is then removed from within the resulting tubular intraluminal graft.

Alternatively, an adhesive such as FEP may be used between the adjacent edges forming the seamline, requiring that the film-wrapped mandrel be heated only adequately to melt the adhesive enough to bond the adjacent edges.

In still another alternative, the PTFE film may be provided with a coating of the adhesive on only one surface of the film. These adhesive-coated films are oriented during wrapping of the mandrel so that the adhesive-coated side of the film faces away from the surface of the mandrel and therefore contacts only adjacent layers of film and does not contact the mandrel. The adhesive is preferably in the form of a discontinuous coating in order to have a minimal effect on the porosity of the completed thin wall intraluminal graft. The adhesive must be biocompatible preferred adhesives are thermoplastics of lower melt point than the crystalline melt point of the PTFE film. Thermoplastic fluoropolymers such as FEP are most preferred. These types of adhesives are activated by placing the film-wrapped mandrel into an oven at a combination of time and temperature adequate to cause melting of the adhesive.

The FEP-coated porous expanded PTFE film is made by a process which comprises the steps of:
a) contacting a porous PTFE film with another layer which is preferably a film of FEP or alternatively of another thermoplastic polymer;
b) heating the composition obtained in step a) to a temperature above the melting point of the thermoplastic polymer;
c) stretching the heated composition of step b) while maintaining the temperature above the melting point of the thermoplastic polymer; and
d) cooling the product of step c).

The adhesive coating on the multiaxially-oriented porous expanded PTFE film may be either continuous (non-porous) or discontinuous (porous) depending primarily on the amount and rate of stretching, the temperature during stretching and the thickness of the adhesive prior to stretching.

Figure 6:
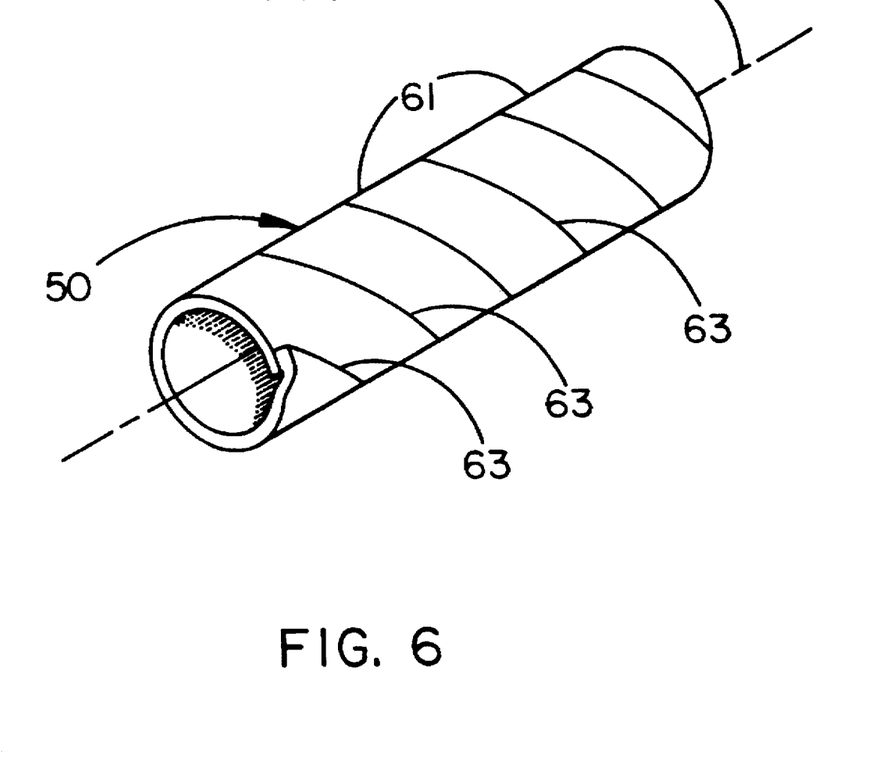
FIG. 6 is a perspective view of an intraluminal graft of the present invention having a radially oriented seamline.

As described by FIG. 6, the intraluminal graft 50 may be formed by wrapping a tape 61, formed by cutting a multiaxially-oriented porous expanded PTFE film into a narrow strip, helically-wrapping the tape 61 around a mandrel and overlapping adjacent edges of the tape to create a helically-oriented seamline 63. The overlapping adjacent edges may be adhered as described previously for the longitudinally-oriented seamlines 51.

Figure 7A:
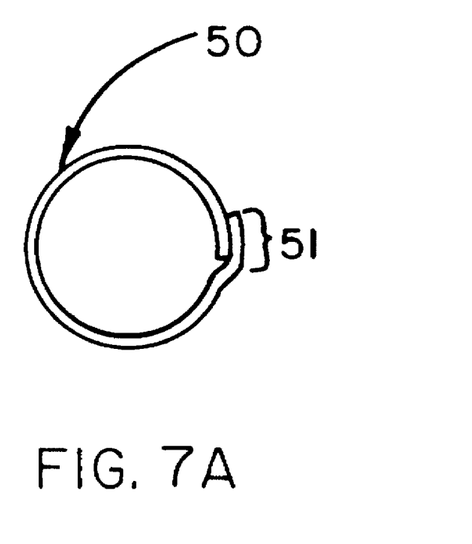
FIGS. 7A, 7B and 7C are cross sectional views of an intraluminal graft of the present invention made from a single layer of film.
Figure 7B:
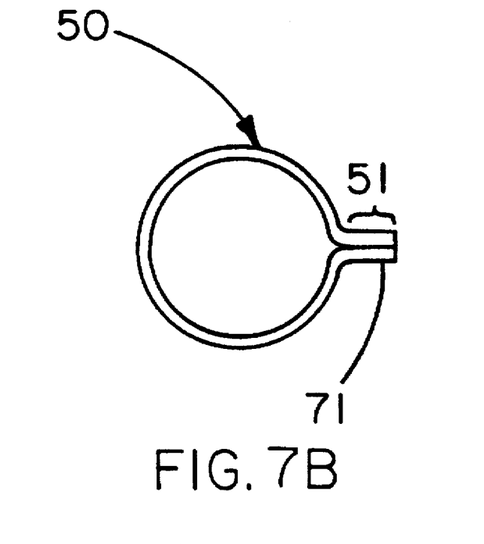
Figure 7C:
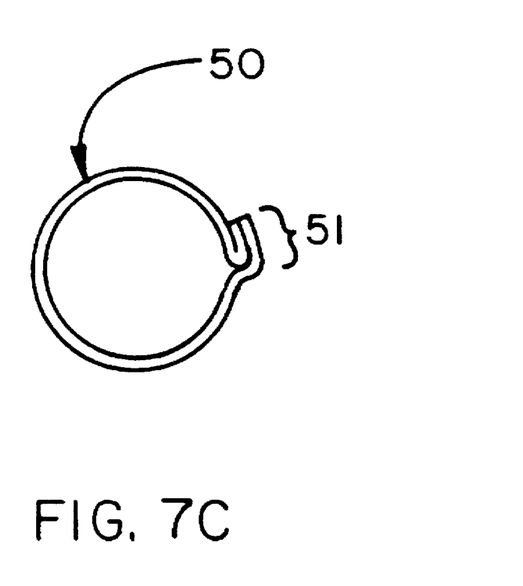

FIG. 7A shows a cross section of the intraluminal graft 50 having a simple overlapped seamline 51. In an alternative embodiment described by the cross sectional view of FIG. 7B, the seamline 51 may be formed as a flange 71 which may optionally be folded over as shown by the cross sectional view of FIG. 7C. The seamlines of FIGS. 78 and 7C are most practical for longitudinally-oriented seamlines; the simple overlapped edge seamline of FIG. 7A is preferred for helically-oriented seamlines.

Figure 8:
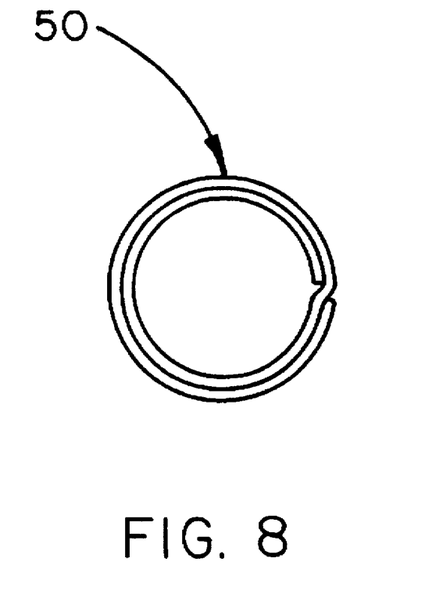
FIG. 8 is a cross sectional view of an intraluminal graft of the present invention made from two layers of film.

As shown by the cross sectional view of FIG. 8, the intraluminal graft may also be made from two or more layers of multiaxially-oriented porous expanded PTFE film by allowing the film to completely overlap itself at least one time. Two or more layer embodiments may be formed by either helically or longitudinally wrapping the film around the mandrel.

Various samples of the intraluminal graft of the present invention were constructed and are described below as examples. The methods used to characterize the fibril lengths of the films used to make the grafts, the wall thicknesses of the films and the resulting grafts, and the method used to mechanically test the integrity of the resulting grafts are as follows.

The fibril lengths of the porous expanded PTFE films referred to herein were estimated mean values obtained by examining scanning electron photomicrographs of these films. For multiaxially-oriented films, these estimates included consideration of fibrils oriented in all directions. The mean fibril lengths of the films used to construct the intraluminal grafts of the present invention are preferred to be within range of about 5 to about 120 microns, although fibril lengths beyond this range may also be useful.

Wall thickness measurements of the finished intraluminal grafts were made by longitudinally slitting the wall of a short length of the tubular graft to create a flat sheet. These wall thickness measurements did not include the overlapped edges of the seamlines. Seamlines are not included in wall thickness measurements unless the width of the seamline is such that the graft is made from two or more layers of film as described by the cross sectional view of FIG. 8. The wall thickness of the flat sheet was measured using a Mitutoyo model no. 2804-10 snap gauge having a part no. 7300 frame, by placing the sheet between the pads of the gauge and gently easing the pads into contact with the sample until the pads were in full contact with the sheet under the full force of the spring-driven snap gauge pads. Film density values were based on the bulk volume of a film sample using the snap-gauge thickness measurement.

Pressure testing of all samples was accomplished by inserting a length of 6 mm outside diameter tubular latex bladder of about 0.4 mm wall thickness into the lumen of the tubular sample to be tested, clamping off one end of the tubular sample and latex bladder assembly with forceps, and applying air pressure for a period of time as described for each example to the tubular sample and bladder assembly. Approximately three seconds was required to achieve the described air pressure level; this three second period was not included in the test period. After the release of pressure, the bladder was removed from the tubular sample and the sample was visually inspected for any resulting damage.

EXAMPLE 1

A multiaxially-oriented porous expanded PTFE film having biaxially-oriented fibrils as described by FIGS. 1 and 3 was used to make an intraluminal graft. The film used was of about 30 micron fibril length, about 10 cm width and about 0.08 mm thickness. A 12 cm long sample of this film was wrapped around a 6 mm diameter stainless steel mandrel forming a longitudinally-oriented seamline as shown by FIGS. 7B and 7C. The biaxially-oriented fibrils of the film were oriented to be parallel to the circumference of the mandrel and parallel to the longitudinal axis of the mandrel. The film edges were adhered by using a hot iron shielded with a thin sheet of polyimide film. The iron, having a surface temperature of about 400° C., was applied by hand against the thin sheet of polyimide film and the length of the seamline. The excess material was then trimmed away with a scalpel leaving an overlapping seamline of about 2 mm width. The film-wrapped mandrel was then placed into an oven set at 381° C. for 6 minutes, after which it was removed from the oven and allowed to cool. The mandrel was then removed from the finished intraluminal graft. A 10 cm length of the intraluminal graft was pressure tested at 1.0 kg/cm$^2$ for 30 seconds without any adverse visible effects.

EXAMPLE 2

A length of 12.5 mm wide tape was cut from the same film used to construct Example 1. The strip of tape was cut so that the biaxially-oriented fibrils of the film were oriented substantially parallel and perpendicular to the length of the tape. The tape was then helically wrapped around the surface of a 6 mm stainless steel mandrel as shown by FIG. 6 to form an intraluminal graft of about 16 cm length. Adjacent tape edges overlapped by about 1 mm. The film-wrapped mandrel was then placed into an oven set at 380° C. for 10 minutes after which it was removed and allowed to cool. The mandrel was then removed from the finished intraluminal graft. A 17 cm length of the graft was then pressure tested at 1.0 kg/cm$^2$ for 3 minutes. The pressure test caused no visible damage to the graft.

EXAMPLE 3

An intraluminal graft was formed from the film described by FIG. 4. This film had a fibril length of about 5 microns, a thickness of about 0.6 mm and a density of 0.3 g/cc. This film is available as a filtration membrane from W. L. Gore & Associates, Inc., Elkton, Md., part no. 10382. A 7 cm length of this film was wrapped around a 6 mm stainless steel mandrel to form a longitudinally-oriented seamline of about 1 mm width as shown by FIG. 7A. A 1 mm wide strip of 0.013 mm thick FEP film was placed between the overlapped edges of the multiaxially-oriented porous PTFE film. The film-covered mandrel was placed into an oven set at 353° C. for 4.5 minutes, removed and allowed to cool. Excess material was trimmed from the 1 mm wide seamline at this time. The mandrel was then removed from the finished intraluminal graft. A 5 cm length of this graft was then pressure tested at 1.0 kg/cm² for 30 seconds without visible damage.

Figure 9A:
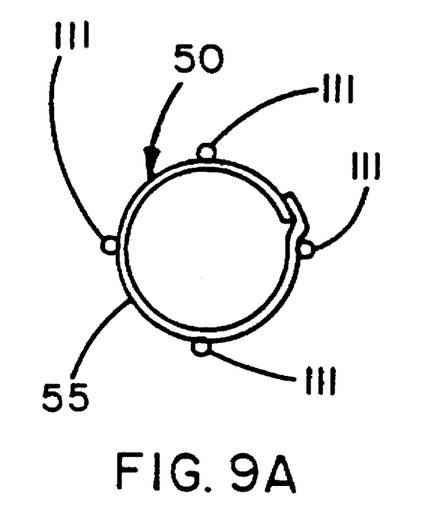
FIGS. 9A, 9B and 9C describe cross sectional views of the intraluminal graft incorporating reinforcing ribs.
Figure 9B:
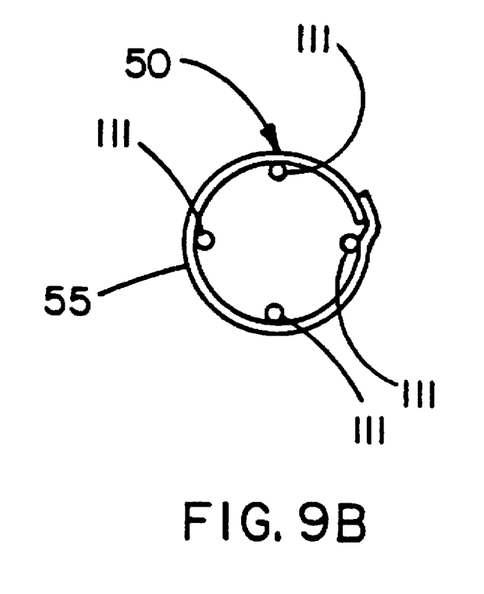
Figure 9C:
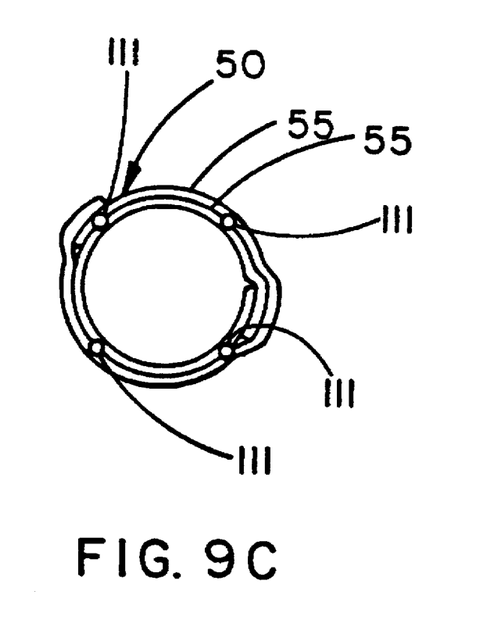
Figure 10:
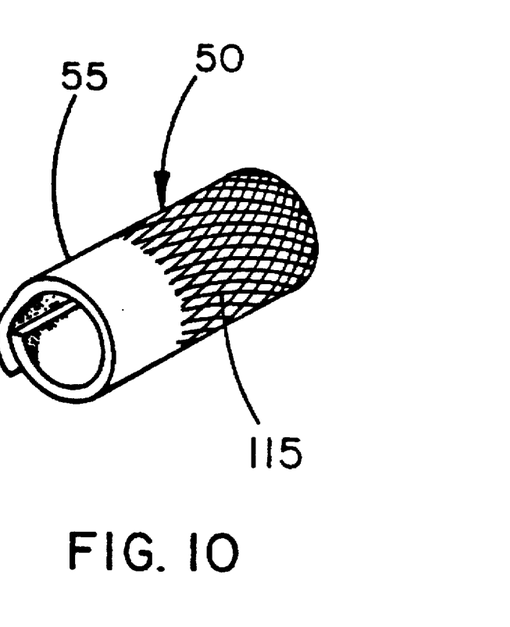
FIG. 10 describes a perspective view of the intraluminal graft incorporating a reinforcing braid.

As previously described, the intraluminal graft may be provided with longitudinal reinforcing ribs in the form of stringers of, for example, FEP or PTFE. FIG. 9A describes a cross sectional view of an intraluminal graft with ribs 111 on the exterior surface. FIG. 9B describes a cross sectional view of an intraluminal graft with ribs 111 on the luminal surface. FIG. 9C shows a cross sectional view having ribs 111 between two layers of film. The ribs are not limited to being oriented parallel to the longitudinal axis of the intraluminal graft, but may also be provided to be oriented substantially circumferential to the tube, for example helically oriented. Alternatively, as shown by FIG. 10 a braid 115 may used as an additional reinforcing component in place of the reinforcing ribs.

We claim:

1. An intraluminal graft comprising a tube having an exterior surface, a luminal surface, ends, and a longitudinal axis, said tube being comprised of at least one layer of porous expanded polytetrafluoroethylene film wherein the porous expanded polytetrafluoroethylene film has an edge extending between the ends of the tube and has a microstructure having fibrils oriented in at least two directions which are substantially perpendicular to each other, and wherein said tube has a wall thickness of greater than about 0.08 mm and less than about 0.25 mm.

2. An intraluminal graft according to claim 1 wherein the tube has a seamline formed by overlapping the edges of the porous expanded polytetrafluoroethylene film.

3. An intraluminal graft according to claim 2 wherein the seamline is substantially parallel to the longitudinal axis of the tube.

4. An intraluminal graft according to claim 2 wherein the seamline is helically oriented with respect to the longitudinal axis of the tube.

5. An intraluminal graft according to claim 1 wherein the tube has a wall thickness of less than about 0.1 mm.

6. An intraluminal graft according to claim 2 wherein the tube has a wall thickness of less than about 0.1 mm.

7. An intraluminal graft according to claim 3 wherein the tube has a wall thickness of less than about 0.1 mm.

8. An intraluminal graft according to claim 4 wherein the tube has a wall thickness of less than about 0.1 mm.

9. An intraluminal graft according to claim 2 wherein the seamline is adhered by an adhesive.

10. An intraluminal graft according to claim 9 wherein the adhesive is fluorinated ethylene propylene.

11. An intraluminal graft according to claim 1 wherein the tube is provided with at least one reinforcing rib.

12. An intraluminal graft according to claim 2 wherein the tube is provided with at least one reinforcing rib.

13. An intraluminal graft according to claim 5 wherein the tube is provided with at least one reinforcing rib.

14. An intraluminal graft according to claim 6 wherein the tube is provided with at least one reinforcing rib.

15. An intraluminal graft according to claim 1 wherein the tube is provided with a reinforcing braid.

16. An intraluminal graft according to claim 2 wherein the tube is provided with a reinforcing braid.

17. An intraluminal graft according to claim 5 wherein the tube is provided with a reinforcing braid.

18. An intraluminal graft according to claim 6 wherein the tube is provided with a reinforcing braid.

* * * * *